(12) United States Patent
Rölle et al.

US010308619B2

(10) Patent No.: US 10,308,619 B2
(45) Date of Patent: Jun. 4, 2019

(54) SUBSTITUTED TRIAZINES AND A METHOD FOR PRODUCING SAME

(71) Applicant: Covestro Deutschland AG, Leverkusen (DE)

(72) Inventors: Thomas Rölle, Leverkusen (DE); Koichi Kawamura, Odenthal (DE); Guiseppe Chiovetta, Hürth (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/738,905

(22) PCT Filed: Jun. 21, 2016

(86) PCT No.: PCT/EP2016/064305
§ 371 (c)(1),
(2) Date: Dec. 21, 2017

(87) PCT Pub. No.: WO2016/207158
PCT Pub. Date: Dec. 29, 2016

(65) Prior Publication Data
US 2018/0186758 A1   Jul. 5, 2018

(30) Foreign Application Priority Data
Jun. 23, 2015   (EP) .................................... 15173235

(51) Int. Cl.
| | | |
|---|---|---|
| C07C 67/02 | (2006.01) | |
| C07D 251/24 | (2006.01) | |
| G11B 7/24044 | (2013.01) | |
| C07C 253/30 | (2006.01) | |
| G03F 7/00 | (2006.01) | |
| G11B 7/245 | (2006.01) | |
| G03F 7/029 | (2006.01) | |
| G03F 7/031 | (2006.01) | |

(52) U.S. Cl.
CPC ............ *C07D 251/24* (2013.01); *C07C 67/02* (2013.01); *C07C 253/30* (2013.01); *G03F 7/001* (2013.01); *G03F 7/029* (2013.01); *G03F 7/031* (2013.01); *G11B 7/245* (2013.01); *G11B 7/24044* (2013.01)

(58) Field of Classification Search
CPC .................................................... C07C 67/02
See application file for complete search history.

(56) References Cited

U.S. PATENT DOCUMENTS

| 3,090,782 A | 5/1963 | Coenen et al. |
| 5,064,959 A | 11/1991 | Pawlowski et al. |
| 5,489,499 A | 2/1996 | Yumoto |
| 6,194,123 B1 | 2/2001 | Smith et al. |
| 7,588,863 B2 | 9/2009 | Takizawa et al. |
| 8,361,678 B2 | 1/2013 | Weiser et al. |
| 9,146,456 B2 | 9/2015 | Berneth et al. |
| 2005/0026081 A1 | 2/2005 | Kawamura |
| 2012/0321998 A1 | 12/2012 | Rölle et al. |
| 2013/0034805 A1 | 2/2013 | Hayashida et al. |
| 2013/0072615 A1 | 3/2013 | Muro et al. |
| 2016/0320695 A1 | 11/2016 | Rölle et al. |

FOREIGN PATENT DOCUMENTS

| DE | 1073662 B | 1/1960 |
| EP | 0223587 A1 | 5/1987 |
| EP | 0332042 A1 | 9/1989 |
| EP | 1457190 A1 | 9/2004 |
| EP | 2172503 A1 | 4/2010 |
| EP | 2450387 A1 | 5/2012 |
| EP | 2450893 A1 | 5/2012 |
| EP | 13198913.9 | 12/2013 |
| EP | 2774921 A1 | 9/2014 |
| WO | WO-2012062655 A2 | 5/2012 |

OTHER PUBLICATIONS

International Search Report for PCT/EP2016/064304 dated Aug. 23, 2016.
International Search Report for PCT/EP2016/064305 dated Sep. 13, 2016.
International Search Report for PCT/EP2016/064313 dated Aug. 1, 2016.
Written Opinion of the International Searching Authority for PCT/EP2016/064304 dated Aug. 23, 2016.
Written Opinion of the International Searching Authority for PCT/EP2016/064305 dated Sep. 13, 2016.
Written Opinion of the International Searching Authority for PCT/EP2016/064313 dated Aug. 1, 2016.
Tobe et al., "Synthesis and Association Behavior of [4.4.4.4.4.4]Metacyclophanedodecayne Derivatives with Interior Binding Groups", *Angew. Chem. Int. Ed.*, vol. 37, No. 9, pp. 1285-1287 (1998).
Loupy et al., "Synthesis of Long Chain Aromatic Esters in a Solvent-Free Procedure Under Microwaves", *Tetrahedron*, vol. 52, No. 19, pp. 6705-6712 (1996).
Barrett et al., "Nucleophilic Substitution Reactions of (Alkoxymethylene) dimethylammonium Chloride", *J. Org. Chem.*, vol. 63, pp. 6273-6280 (1998).
Mahabaleshwara et al., "Novel Biphenyl-Substituted 1,2,4-Oxadiazole Ferroelectric Liquid Crystals: syntheseis and Characterization", *Beilstein J. Org. Chem.*, vol. 11, pp. 233-241 (2015).
Database PubChem Compound [Online], NCBI: Feb. 13, 2015 (Feb. 13, 2015), Database Accession No. CID 89215661.

(Continued)

*Primary Examiner* — Deepak R Rao (74) *Attorney, Agent, or Firm* — Drinker Biddle & Reath LLP (57) ABSTRACT

The present invention provides aromatic 4,6-bis-trichloromethyl-s-triazin-2-yl compounds of formula (I), a process for producing para-disubstituted benzonitriles as precursor to give compounds of formula (I) and a process for the production thereof.

1 Claim, 2 Drawing Sheets

(56) References Cited

OTHER PUBLICATIONS

Markwardt et al., Uber die antifibrinolytische Wirkung von Estern der 4-Aminomethylbenzoesäure (PAMBA), *Eingegangen am* (Jul. 13, 1965).

Dieing et al., "Soluble Substituted µ-Oxo(phthalocyaninato)iron(III) Dimers", *Chem. Ber.*, vol. 128, pp. 589-598, (1995).

Krasik, "Synthesis of Sterically Hindered Esters via Titanium Catalyzed Transesterification", *Tetrahedron Letters*, vol. 39, pp. 4223-4226 (1998).

SUBSTITUTED TRIAZINES AND A METHOD FOR PRODUCING SAME

CROSS-REFERENCE TO RELATED APPLICATIONS

This application is a national stage application (under 35 U.S.C. § 371) of PCT/EP2016/064305, filed Jun. 21, 2016, which claims benefit of European Application No. 15173235.1, filed Jun. 23, 2015, both of which are incorporated herein by reference in their entirety.

The present invention relates to aromatic 4,6-bis-trichloromethyl-s-triazin-2-yl compounds of formula (I), a process for producing para-disubstituted benzonitriles as precursor to give compounds of formula (I) and a process for the production thereof.

BACKGROUND OF THE INVENTION

European application EP13198913.9, unpublished at the priority date of the present invention, discloses light-sensitive photopolymers which comprise polyurethane matrix polymers, an acrylate-based writing monomer and also photoinitiators comprising two coinitiators and a dye. The uses of photopolymers are decisively determined by the refractive index modulation Δn produced by holographic exposure. In holographic exposure, the interference field of signal light beam and reference light beam (that of two plane waves in the simplest case) is mapped into a refractive index grating by the local photopolymerization of writing monomers such as, for example, high-refractive acrylates at loci of high intensity in the interference field. The refractive index grating in the photopolymer (the hologram) contains all the information of the signal light beam. Illuminating the hologram with only the reference light beam will then reconstruct the signal. The strength of the signal thus reconstructed relative to the strength of the incident reference light is called the diffraction efficiency, DE in what follows.

In the simplest case of a hologram resulting from the superposition of two plane waves, the DE is the ratio of the intensity of the light diffracted on reconstruction to the sum total of the intensities of diffracted light and nondiffracted light. The higher the DE, the greater the efficiency of a hologram with regard to the amount of reference light needed to visualize the signal with a fixed brightness.

In order that a very high Δn and DE may be realized for holograms, the matrix polymers and the writing monomers of a photopolymer formulation should in principle be chosen such that there is a very large difference in their refractive indices. One possible way to realize this is to use matrix polymers having a very low refractive index and writing monomers having a very high refractive index. Suitable matrix polymers of low refractive index are, for example, polyurethanes obtainable by reaction of a polyol component with a polyisocyanate component.

In addition to high DE and Δn values, however, another important requirement for holographic media from photopolymer formulations is that the matrix polymers be highly crosslinked in the final medium. When the degree of crosslinking is too low, the medium will lack adequate stability. One consequence of this is to appreciably reduce the quality of holograms inscribed in the media. In the worst case, the holograms may even be subsequently destroyed.

It is further very important, in particular for the large scale industrial production of holographic media from photopolymer formulations, that the photosensitivity be sufficient to achieve large-area exposure with any given source of laser light without loss of index modulation. Particularly the choice of a suitable photoinitiator here is of decisive importance for the properties of the photopolymer.

However, holographic exposure using a continuous source of laser light comes up against technical limits in the case of large-area exposure, since efficient formation of the hologram will always require a certain minimum of light per unit area and the technically available laser power is limited. Large-area exposures at a comparatively low dose of radiation additionally require long exposure times which in turn impose very high requirements on the mechanical damping of the exposure set-up to eliminate vibration.

A further possible way to achieve large-area exposure of holograms consists in using very short pulses of light, for example from pulsed lasers or continuous wave lasers in conjunction with very fast shutters. Pulse durations with pulsed lasers are typically 500 ns or less. Pulse durations with continuous wave lasers and very fast shutters are typically 100 μs or less. In effect, the same amount of energy can be introduced here as with continuous lasers in seconds. Holograms can be written in this way dot by dot. Since pulsed lasers or fast optical shutters are technically available and an exposure set-up of this type has very low requirements with regard to mechanical damping to eliminate vibration, this amounts to a good technical alternative to the above-described set-ups involving continuous lasers for large-area exposure of holograms.

The photopolymers known from European application EP13198913.9 are generally usable for writing holograms with pulsed lasers but a further increase in sensitivity of the photopolymer is desirable for broad industrial utility.

BRIEF SUMMARY OF THE INVENTION

The problem addressed by the present invention was therefore that of providing a compound useful in the production of photopolymers whereinto bright holograms can be written with pulsed lasers by reason of higher photosensitivity.

This problem is solved by a compound of formula (I)

characterized in that X is halogen and $R^1$, $R^2$, $R^3$ and $R^4$ are each independently hydrogen, halogen, alkyl, alkoxy, alkenyl, alkynyl, alkylthio, alkylseleno, wherein $R^1$ and $R^2$ and/or $R^3$ and $R^4$ may combine to form a 3 to 5-membered saturated or unsaturated bridge optionally substituted with up to 2 heteroatoms and $R^5$ is linear $C_5$ to $C_{20}$ alkyl which is optionally substituted in any manner by halogen and/or $C_1$ to $C_{10}$ alkyl and/or $C_1$ to $C_{10}$ alkoxy and in which up to six carbon atoms may be replaced by oxygen, in which case at least two carbon atoms shall be present between two oxygen atoms and the $R^5$ moiety starts with at least two carbon atoms, wherein the terminal methyl group of the linear $C_5$ to $C_{20}$ alkyl moiety shall be unsubstituted.

This is because it was found that, surprisingly, media which comprise a compound of formula (I) according to the present invention have a higher level of photosensitivity and hence are very useful for exposure using pulsed lasers.

In one preferred embodiment of the invention, the X moiety represents chlorine. In a further embodiment of the invention, $R^1$, $R^2$, $R^3$ and $R^4$ are each hydrogen. $R^5$ may in one embodiment of the invention be linear $C_6$ to $C_{20}$ alkyl which is optionally substituted in any manner by halogen and/or $C_1$ to $C_4$ alkyl and/or $C_1$ to $C_4$ alkoxy and in which up to six carbon atoms may be replaced by oxygen, in which case at least two carbon atoms shall be present between two oxygen atoms and the $R^5$ moiety starts with at least two carbon atoms, wherein the terminal methyl group of the linear $C_6$ to $C_{20}$ alkyl moiety shall be unsubstituted.

It is likewise preferable when the compound of formula (I) has an X moiety representing chlorine, the moieties $R^1$, $R^2$, $R^3$ and $R^4$ each representing H and the $R^5$ representing 2-ethylhexanol.

According to EP 0332 042 A2, 4,6-bis-trichloromethyl-s-triazin-2-yl-phenyl derivatives are obtainable from aromatic nitriles and trichloroacetonitrile by cyclocotrimerization. To this end, the 3- or 4-cyano-substituted methyl benzoate or cinnamate esters are reacted with trichloroacetonitrile and then the resultant 4,6-bistrichloromethyl-s-triazine-substituted methyl benzoate or cinnamate ester is transesterified in a costly and inconvenient manner involving in some instances multiple steps.

DETAILED DESCRIPTION OF THE INVENTION

The problem addressed by the present invention was therefore further that of providing a simple economical process for preparing compounds (I) and precursors thereof.

This problem was solved by
a process for preparing para-disubstituted benzoic ester nitriles of formula (IV)

where $R^1$ to $R^5$ are each as defined under formula (I), $R^6$ is methyl or ethyl or isomeric propyl, and A is a catalyst A, in a one-pot process wherein component (III) is used in excess, components V, III and IV are distillatively removed in the stated order in three steps by adjusting the pressure and the temperature, and the difference in the boiling points of compounds (V) and (III) and in the boiling points of compounds (III) and (IV) is not less than 50° C. in either case.

In said one-pot process, an ester of formula (II) where $R^1$ to $R^4$ are each defined under formula (I) and $R^6$ are methyl or ethyl or the isomeric propyls is converted in the presence of an alcohol (III) where $R^5$ is as defined above and in the presence of a catalyst A, by heating in a first step at an internal temperature of 100-150° C. and a pressure of 300-1000 mbar with an excess of 1.1 to 10 equivalents of (III) until the conversion of (II) is complete and distillatively removing (V) from the reaction mixture and a subsequent step of distillatively removing excess alcohol (III) at a overhead temperature of 50-150° C. and a pressure of 1-300 mbar followed in a subsequent step by the distillation of product (IV) at an overhead temperature of 100-250° C. and a pressure of 0.01-1 mbar, leaving catalyst A behind in the pot.

Step 1 utilizes an internal temperature of 100-150° C., preferably 110-145° C., more preferably 120-140° C. at a pressure of 300-1000 mbar, preferably 350-800 mbar, more preferably 400-600 mbar with an excess of 1.1 to 10 equivalents of (III), preferably of 1.2 to 5 equivalents, more preferably of 1.3 to 2 equivalents.

The second step utilizes an overhead temperature of 50-150° C., preferably 60-125° C., more preferably 70-100° C. and a pressure of 1-300 mbar, preferably 3-100 mbar, more preferably 5-50 mbar.

The third step utilizes an overhead temperature of 100-250° C., preferably of 125-240° C., more preferably of 150-230° C. and a pressure of 0.01-1 mbar, preferably of 0.02-0.5 mbar.

Alcohol (III) is suitably any compound having not less than five and up to 20 aliphatic optionally halogen- or oxygen-substituted carbon atoms bearing at least one methyl group. Preference is given to compounds having not less than six and up to 15 aliphatic optionally halogen- or oxygen-substituted carbon atoms bearing at least one methyl group. Particular preference is given to compounds having not less than seven and up to 10 aliphatic optionally halogen- or oxygen-substituted carbon atoms bearing at least one methyl group.

Catalyst A is suitably, the fundamentally described in Methoden der organischen Chemie (Houben-Weyl), Volume E5, 1, III.a) γ, $γ_1$ (pp. 702 ff, Pielartzik, Irmscher-Pielartzik and Eicher), catalysts such as protic acids, basic catalysts (alkanoates, anion exchangers), titanium(IV) and zirconium (IV) alkanoates, alkoxytrialkyltin and also copper alkanoate/triphenylphosphane complexes. Preferably, the catalysts are in liquid form, have a higher boiling point than the desired product and are effective in low concentration in ensuring rapid and complete conversion. Higher titanium(IV) and zirconium(IV) alkanoates are therefore particularly preferable. Particular preference is given especially to higher titanium(IV) and zirconium (IV) alkanoates wherein the alkanoate corresponds to that of compound (III).

It is further preferable for catalyst A to be employed in an amount of 0.0001 to 0.1 equivalent relative to employed compound (II), more preferably of 0.0005 to 0.01 equivalent and yet more preferably 0.001 to 0.005 equivalent.

The invention further provides a process for preparing compounds (I) which comprises utilizing the one-pot process to prepare para-disubstituted benzonitriles of formula (IV) in a first step and reacting the resulting para-disubstituted benzonitrile with trihaloacetonitrile in a second step.

The invention further provides a photopolymer formulation comprising a photopolymerizable component and at least one compound of formula (I).

In one embodiment of the photopolymer formulation, it comprises matrix polymers, at least one writing monomer and a photoinitiator system comprising at least one compound of formula (I).

The matrix polymers of the photopolymer formulation according to the present invention may be particularly in a crosslinked state and more preferably in a three-dimensionally crosslinked state.

It is also advantageous for the matrix polymers to be polyurethanes, in which case the polyurethanes may be obtainable in particular by reacting at least one polyisocyanate component a) with at least one isocyanate-reactive component b).

The polyisocyanate component a) preferably comprises at least one organic compound having at least two NCO groups. These organic compounds may especially be monomeric di- and triisocyanates, polyisocyanates and/or NCO-functional prepolymers. The polyisocyanate component a) may also contain or consist of mixtures of monomeric di- and triisocyanates, polyisocyanates and/or NCO-functional prepolymers.

Monomeric di- and triisocyanates used may be any of the compounds that are well known per se to those skilled in the art, or mixtures thereof. These compounds may have aromatic, araliphatic, aliphatic or cycloaliphatic structures. The monomeric di- and triisocyanates may also comprise minor amounts of monoisocyanates, i.e. organic compounds having one NCO group.

Examples of suitable monomeric di- and triisocyanates are butane 1,4-diisocyanate, pentane 1,5-diisocyanate, hexane 1,6-diisocyanate (hexamethylene diisocyanate, HDI), 2,2,4-trimethylhexamethylene diisocyanate and/or 2,4,4-trimethylhexamethylene diisocyanate (TMDI), isophorone diisocyanate (IPDI), 1,8-diisocyanato-4-(isocyanatomethyl)octane, bis(4,4'-isocyanatocyclohexyl)methane and/or bis(2',4-isocyanatocyclohexyl)methane and/or mixtures thereof having any isomer content, cyclohexane 1,4-diisocyanate, the isomeric bis(isocyanate-methyl)cyclohexanes, 2,4- and/or 2,6-diisocyanato-1-r-methylcyclohexane (hexahydrotolylene 2,4- and/or 2,6-diisocyanate, $H_6$-TDI), phenylene 1,4-diisocyanate, tolylene 2,4- and/or 2,6-diisocyanate (TDI), naphthylene 1,5-diisocyanate (NDI), diphenylmethane 2,4'- and/or 4,4'-diisocyanate (MDI), 1,3-bis(isocyanatomethyl)benzene (XDI) and/or the analogous 1,4 isomers or any desired mixtures of the aforementioned compounds.

Suitable polyisocyanates are compounds which have urethane, urea, carbodiimide, acylurea, amide, isocyanurate, allophanate, biuret, oxadiazinetrione, uretdione and/or iminooxadiazinedione structures and are obtainable from the aforementioned di- or triisocyanates.

More preferably, the polyisocyanates are oligomerized aliphatic and/or cycloaliphatic di- or triisocyanates, it being possible to use especially the above aliphatic and/or cycloaliphatic di- or triisocyanates.

Very particular preference is given to polyisocyanates having isocyanurate, uretdione and/or iminooxadiazinedione structures, and biurets based on HDI or mixtures thereof.

Suitable prepolymers contain urethane and/or urea groups, and optionally further structures formed through modification of NCO groups as specified above. Prepolymers of this kind are obtainable, for example, by reaction of the abovementioned monomeric di- and triisocyanates and/or polyisocyanates a1) with isocyanate-reactive compounds b1).

Isocyanate-reactive compounds b1) used may be alcohols, amino or mercapto compounds, preferably alcohols. These may especially be polyols. Most preferably, isocyanate-reactive compounds b1) used may be polyester polyols, polyether polyols, polycarbonate polyols, poly(meth)acrylate polyols and/or polyurethane polyols.

Suitable polyester polyols are, for example, linear polyester diols or branched polyester polyols, which can be obtained in a known manner by reaction of aliphatic, cycloaliphatic or aromatic di- or polycarboxylic acids or anhydrides thereof with polyhydric alcohols of OH functionality ≥2. Examples of suitable di- or polycarboxylic acids are polybasic carboxylic acids such as succinic acid, adipic acid, suberic acid, sebacic acid, decanedicarboxylic acid, phthalic acid, terephthalic acid, isophthalic acid, tetrahydrophthalic acid or trimellitic acid, and acid anhydrides such as phthalic anhydride, trimellitic anhydride or succinic anhydride, or any desired mixtures thereof. The polyester polyols may also be based on natural raw materials such as castor oil. It is likewise possible that the polyester polyols are based on homo- or copolymers of lactones, which can preferably be obtained by addition of lactones or lactone mixtures, such as butyrolactone, ε-caprolactone and/or methyl-ε-caprolactone onto hydroxy-functional compounds such as polyhydric alcohols of OH functionality ≥2, for example of the abovementioned type.

Examples of suitable alcohols are all polyhydric alcohols, for example the $C_2$-$C_{12}$ diols, the isomeric cyclohexanediols, glycerol or any desired mixtures thereof.

Suitable polycarbonate polyols are obtainable in a manner known per se by reaction of organic carbonates or phosgene with diols or diol mixtures.

Suitable organic carbonates are dimethyl, diethyl and diphenyl carbonate.

Suitable diols or mixtures comprise the polyhydric alcohols of OH functionality ≥2 mentioned per se in the context of the polyester segments, preferably butane-1,4-diol, hexane-1,6-diol and/or 3-methylpentanediol. It is also possible to convert polyester polyols to polycarbonate polyols.

Suitable polyether polyols are polyaddition products, optionally of blockwise structure, of cyclic ethers onto OH- or NH-functional starter molecules.

Suitable cyclic ethers are, for example, styrene oxides, ethylene oxide, propylene oxide, tetrahydrofuran, butylene oxide, epichlorohydrin, and any desired mixtures thereof.

Starters used may be the polyhydric alcohols of OH functionality ≥2 mentioned per se in the context of the polyester polyols, and also primary or secondary amines and amino alcohols.

Preferred polyether polyols are those of the aforementioned type based exclusively on propylene oxide, or random or block copolymers based on propylene oxide with further 1-alkylene oxides. Particular preference is given to propylene oxide homopolymers and random or block copolymers containing oxyethylene, oxypropylene and/or oxybutylene units, where the proportion of the oxypropylene units based on the total amount of all the oxyethylene, oxypropylene and oxybutylene units amounts to at least 20% by weight, preferably at least 45% by weight. Oxypropylene and oxybutylene here encompasses all the respective linear and branched $C_3$ and $C_4$ isomers.

Additionally suitable as constituents of the polyol component b1), as polyfunctional, isocyanate-reactive compounds, are also low molecular weight (i.e. with molecular weights ≤500 g/mol), short-chain (i.e. containing 2 to 20 carbon atoms), aliphatic, araliphatic or cycloaliphatic di-, tri- or polyfunctional alcohols.

These may, for example, in addition to the abovementioned compounds, be neopentyl glycol, 2-ethyl-2-butylpropanediol, trimethylpentanediol, positionally isomeric diethyloctanediols, cyclohexanediol, 1,4- cyclohexanedimethanol, 1,6-hexanediol, 1,2- and 1,4-cyclohexanediol, hydrogenated bisphenol A, 2,2-bis(4-hydroxycyclohexyl)propane or 2,2-dimethyl-3-hydroxypropyl 2,2-dimethyl-3-hydroxypropionate. Examples of suitable triols are trimethylolethane, trimethylolpropane or glycerol. Suitable higher-functionality alcohols are di(trimethylolpropane), pentaerythritol, dipentaerythritol or sorbitol.

It is especially preferable when the polyol component is a difunctional polyether, polyester, or a polyether-polyester block copolyester or a polyether-polyester block copolymer having primary OH functions.

It is likewise possible to use amines as isocyanate-reactive compounds b1). Examples of suitable amines are ethylenediamine, propylenediamine, diaminocyclohexane, 4,4'-dicyclohexylmethane-diamine, isophoronediamine (IPDA), difunctional polyamines, for example the Jeffamines®, amine-terminated polymers, especially having number-average molar masses ≤10 000 g/mol. Mixtures of the aforementioned amines can likewise be used.

It is likewise possible to use amino alcohols as isocyanate-reactive compounds b1). Examples of suitable amino alcohols are the isomeric aminoethanols, the isomeric aminopropanols, the isomeric aminobutanols and the isomeric aminohexanols, or any desired mixtures thereof.

All the aforementioned isocyanate-reactive compounds b1) can be mixed with one another as desired.

It is also preferable when the isocyanate-reactive compounds b1) have a number-average molar mass of ≥200 and ≤10 000 g/mol, further preferably ≥500 and ≤8000 g/mol and most preferably ≥800 and ≤5000 g/mol. The OH functionality of the polyols is preferably 1.5 to 6.0, more preferably 1.8 to 4.0.

The prepolymers of the polyisocyanate component a) may especially have a residual content of free monomeric di- and triisocyanates of <1% by weight, more preferably <0.5% by weight and most preferably <0.3% by weight.

It is optionally also possible that the polyisocyanate component a) contains, entirely or in part, organic compound whose NCO groups have been fully or partly reacted with blocking agents known from coating technology. Example of blocking agents are alcohols, lactams, oximes, malonic esters, pyrazoles, and amines, for example butanone oxime, diisopropylamine, diethyl malonate, ethyl acetoacetate, 3,5-dimethylpyrazole, ε-caprolactam, or mixtures thereof.

It is especially preferable when the polyisocyanate component a) comprises compounds having aliphatically bonded NCO groups, aliphatically bonded NCO groups being understood to mean those groups that are bonded to a primary carbon atom. The isocyanate-reactive component b) preferably comprises at least one organic compound having an average of at least 1.5 and preferably 2 to 3 isocyanate-reactive groups. In the context of the present invention, isocyanate-reactive groups are regarded as being preferably hydroxyl, amino or mnercapto groups.

The isocyanate-reactive component may especially comprise compounds having a numerical average of at least 1.5 and preferably 2 to 3 isocyanate-reactive groups.

Suitable polyfunctional isocyanate-reactive compounds of component b) are for example the above-described compounds b1).

In a further preferred embodiment, the writing monomer c) comprises or consists of at least one mono- and/or one multifunctional writing monomer. Further preferably, the writing monomer may comprise or consist of at least one mono- and/or one multifunctional (meth)acrylate writing monomer. Most preferably, the writing monomer may comprise or consist of at least one mono- and/or one multifunctional urethane (meth)acrylate.

Suitable acrylate writing monomers are especially compounds of the general formula (VI)

in which n≥1 and n≤4 and $R^7$ is a linear, branched, cyclic or heterocyclic organic radical which is unsubstituted or else optionally substituted by heteroatoms and/or $R^8$ is hydrogen or a linear, branched, cyclic or heterocyclic organic radical which is unsubstituted or else optionally substituted by heteroatoms. More preferably, $R^8$ is hydrogen or methyl and/or $R^7$ is a linear, branched, cyclic or heterocyclic organic radical which is unsubstituted or else optionally substituted by heteroatoms.

Acrylates and methacrylates refer, respectively, to esters of acrylic acid and methacrylic acid. Examples of acrylates and methacrylates usable with preference are phenyl acrylate, phenyl methacrylate, phenoxyethyl acrylate, phenoxyethyl methacrylate, phenoxyethoxyethyl acrylate, phenoxyethoxyethyl methacrylate, phenylthioethyl acrylate, phenylthioethyl methacrylate, 2-naphthyl acrylate, 2-naphthyl methacrylate, 1,4-bis(2-thionaphthyl)-2-butyl acrylate, 1,4-bis(2-thionaphthyl)-2-butyl methacrylate, bisphenol A diacrylate, bisphenol A dimethacrylate, and the ethoxylated analogue compounds thereof, N-carbazolyl acrylates.

Urethane acrylates are understood to mean compounds having at least one acrylic ester group and at least one urethane bond. Compounds of this kind can be obtained, for example, by reacting a hydroxy-functional acrylate or methacrylate with an isocyanate-functional compound.

Examples of isocyanate-functional compounds usable for this purpose are monoisocyanates, and the monomeric diisocyanates, triisocyanates and/or polyisocyanates mentioned under a). Examples of suitable monoisocyanates are phenyl isocyanate, the isomeric methylthiophenyl isocyanates. Di-, tri- or polyisocyanates have been mentioned above, and also triphenylmethane 4,4',4"-triisocyanate and tris(p-isocyanatophenyl) thiophosphate or derivatives thereof with urethane, urea, carbodiimide, acylurea, isocyanurate, allophanate, biuret, oxadiazinetrione, uretdione, iminooxadiazinedione structure and mixtures thereof. Preference is given to aromatic di-, tri- or polyisocyanates.

Useful hydroxy-functional acrylates or methacrylates for the preparation of urethane acrylates include, for example, compounds such as 2-hydroxyethyl (meth)acrylate, polyethylene oxide mono(meth)acrylates, polypropylene oxide mono(meth)acrylates, polyalkylene oxide mono(meth)acrylates, poly(ε-caprolactone) mono(meth)acrylates, for example Tone® M100 (Dow, Schwalbach, DE), 2-hydroxypropyl (meth)acrylate, 4-hydroxybutyl (meth)acrylate, 3-hydroxy-2,2-dimethylpropyl (meth)acrylate, hydroxypropyl (meth)acrylate, 2-hydroxy-3-phenoxypropyl acrylate, the hydroxy-functional mono-, di- or tetraacrylates of polyhydric alcohols such as trimethylolpropane, glycerol, pentaerythritol, dipentaerythritol, ethoxylated, propoxylated or alkoxylated trimethylolpropane, glycerol, pentaerythritol, dipentaerythritol or the technical mixtures thereof. Preference is given to 2-hydroxyethyl acrylate, hydroxypropyl acrylate, 4-hydroxybutyl acrylate and poly(ε-caprolactone) mono(meth)acrylate.

It is likewise possible to use the fundamentally known hydroxyl-containing epoxy (meth)acrylates having OH contents of 20 to 300 mg KOH/g or hydroxyl-containing polyurethane (meth)acrylates having OH contents of 20 to 300 mg KOH/g or acrylated polyacrylates having OH contents of 20 to 300 mg KOH/g and mixtures thereof, and mixtures with hydroxyl-containing unsaturated polyesters and mixtures with polyester (meth)acrylates or mixtures of hydroxyl-containing unsaturated polyesters with polyester (meth)acrylates.

Preference is given especially to urethane acrylates obtainable from the reaction of tris(p-isocyanatophenyl) thiophosphate and/or m-methylthiophenyl isocyanate with alcohol-functional acrylates such as hydroxyethyl (meth)acrylate, hydroxypropyl (meth)acrylate and/or hydroxybutyl (meth)acrylate.

It is likewise possible that the writing monomer comprises or consists of further unsaturated compounds such as α,β-unsaturated carboxylic acid derivatives, for example maleates, fumarates, maleimides, acrylamides, and also vinyl ethers, propenyl ethers, allyl ethers and compounds containing dicyclopentadienyl units, and also olefinically unsaturated compounds, for example styrene, α-methylstyrene, vinyltoluene and/or olefins.

Photoinitiators of component d) are compounds activatable typically by means of actinic radiation, which can trigger polymerization of the writing monomers. In the case of the photoinitiators, a distinction can be made between unimolecular (type I) and bimolecular (type II) initiators. In addition, they are distinguished by their chemical nature as photoinitiators for free-radical, anionic, cationic or mixed types of polymerization.

Type I photoinitiators (Norrish type I) for free-radical photopolymerization form free radicals on irradiation through unimolecular bond scission. Examples of type I photoinitiators are triazines, oximes, benzoin ethers, benzil ketals, bisimidazoles, aroylphosphine oxides, sulphoniunm salts and iodonium salts.

Type II photoinitiators (Norrish type II) for free-radical polymerization consist of a dye as sensitizer and a coinitiator, and undergo a bimolecular reaction on irradiation with light matched to the dye. First of all, the dye absorbs a photon and transfers energy from an excited state to the coinitiator. The latter releases the polymerization-triggering free radicals through electron or proton transfer or direct hydrogen abstraction.

In the context of this invention, preference is given to using type II photoinitiators.

Photoinitiator systems of this kind are described in principle in EP 0 223 587 A and consist preferably of a mixture of one or more dyes with ammonium alkylarylborate(s).

Suitable dyes which, together with an ammonium alkylarylborate, form a type II photoinitiator are the cationic dyes described in WO 2012062655, in combination with the anions likewise described therein.

Cationic dyes are preferably understood to mean those from the following classes: acridine dyes, xanthene dyes, thioxanthene dyes, phenazine dyes, phenoxazine dyes, phenothiazine dyes, tri(het)arylmethane dyes—especially diamino- and triamino(het)arylmethane dyes, mono-, di-, tri- and pentamethinecyanine dyes, hemicyanine dyes, externally cationic merocyanine dyes, externally cationic neutrocyanine dyes, zeromethine dyes—especially naphtholactam dyes, streptocyanine dyes. Dyes of this kind are described, for example, in H. Berneth in Ullmann's Encyclopedia of Industrial Chemistry, Azine Dyes, Wiley-VCH Verlag, 2008, H. Berneth in Ullmann's Encyclopedia of Industrial Chemistry, Methine Dyes and Pigments, Wiley-VCH Verlag, 2008, T. Gessner, U. Mayer in Ullmann's Encyclopedia of Industrial Chemistry, Triarylmethane and Diarylmethane Dyes, Wiley-VCH Verlag, 2000.

Particular preference is given to phenazine dyes, phenoxazine dyes, phenothiazine dyes, tri(het)arylmethane dyes—especially diamino- and triamino(het)arylmethane dyes, mono-, di-, tri- and pentamethinecyanine dyes, hemicyanine dyes, zeromethine dyes—especially naphtholactam dyes, streptocyanine dyes.

Examples of cationic dyes are Astrazon Orange G, Basic Blue 3, Basic Orange 22, Basic Red 13, Basic Violet 7, Methylene Blue, New Methylene Blue, Azure A, 2,4-diphenyl-6-(4-methoxyphenyl)pyrylium, Safranin O, Astraphloxin, Brilliant Green, Crystal Violet, Ethyl Violet and thionine.

Preferred anions are especially $C_8$- to $C_{25}$-alkanesulphonate, preferably $C_{13}$- to $C_{25}$-alkanesulphonate, $C_3$- to $C_{18}$-perfluoroalkanesulphonate, $C_4$- to $C_{18}$-perfluoroalkanesulphonate bearing at least 3 hydrogen atoms in the alkyl chain, $C_9$- to $C_{25}$-alkanoate, $C_9$- to $C_{25}$-alkenoate, $C_8$- to $C_{25}$-alkylsulphate, preferably $C_{13}$- to $C_{25}$-alkylsulphate, $C_8$- to $C_{25}$-alkenylsulphate, preferably $C_{13}$- to $C_{25}$-alkenylsulphate, $C_3$- to $C_{18}$-perfluoroalkylsulphate, $C_4$- to $C_{18}$-perfluoroalkylsulphate bearing at least 3 hydrogen atoms in the alkyl chain, polyether sulphates based on at least 4 equivalents of ethylene oxide and/or 4 equivalents of propylene oxide, bis($C_4$- to $C_{25}$-alkyl, $C_5$- to $C_7$-cycloalkyl, $C_3$- to $C_8$-alkenyl or $C_7$- to $C_{11}$-aralkyl)sulphosuccinate, bis-$C_2$- to $C_{10}$-alkylsulphosuccinate substituted by at least 8 fluorine atoms, $C_8$- to $C_{25}$-alkylsulphoacetates, benzenesulphonate substituted by at least one radical from the group of halogen, $C_4$- to $C_{25}$-alkyl, perfluoro-$C_1$- to $C_8$-alkyl and/or $C_1$- to $C_{12}$-alkoxycarbonyl, naphthalene- or biphenylsulphonate optionally substituted by nitro, cyano, hydroxyl, $C_1$- to $C_{25}$-alkyl, $C_1$- to $C_{12}$-alkoxy, amino, $C_1$- to $C_{12}$-alkoxycarbonyl or chlorine, benzene-, naphthalene- or biphenyldisulphonate optionally substituted by nitro, cyano, hydroxyl, $C_1$- to $C_{25}$-alkyl, $C_1$- to $C_{12}$-alkoxy, $C_1$- to $C_{12}$-alkoxycarbonyl or chlorine, benzoate substituted by dinitro, $C_6$- to $C_{25}$-alkyl, $C_4$- to $C_{12}$-alkoxycarbonyl, benzoyl, chlorobenzoyl or toluoyl, the anion of naphthalenedicarboxylic acid, diphenyl ether disulphonate, sulphonated or sulphated, optionally at least monounsaturated $C_8$- to $C_{25}$-fatty acid esters of aliphatic $C_1$- to $C_8$-alcohols or glycerol, bis(sulpho-$C_2$- to $C_6$-alkyl) $C_3$- to $C_{12}$-alkanedicarboxylates, bis(sulpho-$C_2$- to $C_6$-alkyl) itaconates, (sulpho-$C_2$- to $C_6$-alkyl) $C_6$- to $C_{18}$-alkanecarboxylates, (sulpho-$C_2$- to $C_6$-alkyl) acrylates or methacrylates, triscatechol phosphate optionally substituted by up to 12 halogen radicals, an anion from the group of tetraphenylborate, cyanotriphenylborate, tetraphenoxyborate, $C_4$- to $C_{12}$-alkyltriphenylborate, wherein the phenyl or phenoxy radicals may be substituted by halogen, $C_1$- to $C_4$-alkyl and/or $C_1$- to $C_4$-alkoxy, $C_4$- to $C_{12}$-alkyltrinaphthylborate, tetra-$C_1$- to $C_{20}$-alkoxyborate, 7,8- or 7,9-dicarba-nido-undecaborate(1-) or (2-), which are optionally substituted on the boron and/or carbon atoms by one or two $C_1$- to $C_{12}$-alkyl or phenyl groups, dodecahydrodicarbadodecaborate(2-) or B—$C_1$- to $C_{12}$-alkyl-C-phenyldodecahydrodicarbadodecaborate(1-), where, in the case of polyvalent anions such as naphthalenedisulphonate, $A^-$ represents one equivalent of this anion, and where the alkane and alkyl groups may be branched and/or may be substituted by halogen, cyano, methoxy, ethoxy, methoxycarbonyl or ethoxycarbonyl.

It is also preferable when the anion $A^-$ of the dye has an AClogP in the range from 1 to 30, more preferably in the range from 1 to 12 and especially preferably in the range from 1 to 6.5. AClogP is computed after J. Comput. Aid. [mol %] Des. 2005, 19, 453; Virtual Computational Chemistry Laboratory, http://www.vcclab.org.

Suitable ammonium alkylarylborates are, for example (Cunningham et al., RadTech'98 North America UV/EB Conference Proceedings, Chicago, Apr. 19-22, 1998): tetrabutylammonium triphenylhexylborate, tetrabutylammonium triphenylbutylborate, tetrabutylammonium trinaphthylhexylborate, tetrabutylammonium tris(4-tert-butyl)phenylbutylborate, tetrabutylammonium tris(3-fluorophenyl)hexylborate hexylborate ([191726-69-9], CGI 7460, product from BASF SE, Basle, Switzerland), 1-methyl-3-octylimidazolium dipentyldiphenylborate and tetrabutylammonium tris (3-chloro-4-methylphenyl)hexylborate ([1147315-11-4], CGI 909, product from BASF SE, Basle, Switzerland).

It may be advantageous to use mixtures of these photoinitiators. According to the radiation source used, the type and concentration of photoinitiator has to be adjusted in the manner known to those skilled in the art. Further details are described, for example, in P. K. T. Oldring (Ed.), Chemistry & Technology of UV & EB Formulations For Coatings, Inks & Paints, vol. 3, 1991, SITA Technology, London, p. 61-328.

It is most preferable when the photoinitiator comprises a combination of dyes whose absorption spectra at least partly cover the spectral range from 400 to 800 nm, with at least one coinitiator matched to the dyes.

It is also preferable when at least one photoinitiator suitable for a laser light colour selected from blue, yellow, green and red is present in the photopolymer formulation.

It is also further preferable when the photopolymer formulation contains one suitable photoinitiator each for at least two laser light colours selected from blue, green and red.

Finally, it is most preferable when the photopolymer formulation contains one suitable photoinitiator for each of the laser light colours blue, green and red.

In a further preferred embodiment, the photopolymer formulation additionally contains urethanes as additives, in which case the urethanes may especially be substituted by at least one fluorine atom.

Preferably, the urethanes may have the general formula (VII)

(VII)

in which m≥1 and m≤8 and $R^9$, $R^{10}$ and $R^{11}$ are linear, branched, cyclic or heterocyclic organic radicals which are unsubstituted or else optionally substituted by heteroatoms and/or $R^{10}$, $R^{11}$ are each independently hydrogen, in which case preferably at least one of the $R^9$, $R^{10}$, $R^{11}$ radicals is substituted by at least one fluorine atom and, more preferably, $R^9$ is an organic radical having at least one fluorine atom. More preferably, $R^{10}$ is a linear, branched, cyclic or heterocyclic organic radical which is unsubstituted or else optionally substituted by heteroatoms, for example fluorine.

The present invention further provides a photopolymer comprising a photopolymer formulation, in particular comprising matrix polymers, writing monomer and a photoinitiator system and further comprising a compound of formula (I).

The matrix polymers of the photopolymer formulation according to the present invention may be particularly in a crosslinked state and more preferably in a three-dimensionally crosslinked state.

It is also advantageous for the matrix polymers to be polyurethanes, in which case the polyurethanes may be obtainable in particular by reacting at least one polyisocyanate component with at least one isocyanate-reactive component.

The above remarks concerning further preferred embodiments of the photopolymer formulation according to the present invention also apply mutatis mutandis to the photopolymer of the present invention.

The invention also provides a holographic medium particularly in the form of a film comprising a photopolymer of the present invention or obtainable by using a photopolymer formulation of the present invention. The invention yet further provides for the use of a photopolymer formulation of the present invention in the production of holographic media.

In one preferred embodiment of the holographic medium according to the present invention, holographic information has been exposed into same.

The inventive holographic media can be processed into holograms by means of appropriate exposure processes for optical applications over the entire visible and in the near UV range (300-800 nm). Visual holograms include all holograms which can be recorded by methods known to those skilled in the art. These include in-line (Gabor) holograms, off-axis holograms, full-aperture transfer holograms, white light transmission holograms ("rainbow holograms"), Denisyuk holograms, off-axis reflection holograms, edge-lit holograms and holographic stereogramrs. Preference is given to reflection holograms, Denisyuk holograms, transmission holograms.

Possible optical functions of the holograms which can be produced with the inventive photopolymer formulations correspond to the optical functions of light elements such as lenses, mirrors, deflecting mirrors, filters, diffuser lenses, diffraction elements, diffusers light guides, waveguides, projection lenses and/or masks. It is likewise possible for combinations of these optical functions to be combined in one hologram independently of each other. These optical elements frequently have a frequency selectivity according to how the holograms have been exposed and the dimensions of the hologram.

In addition, by means of the inventive media, it is also possible to produce holographic images or representations, for example for personal portraits, biometric representations in security documents, or generally of images or image structures for advertising, security labels, brand protection, branding, labels, design elements, decorations, illustrations, collectable cards, images and the like, and also images which can represent digital data, including in combination with the products detailed above. Holographic images can have the impression of a three-dimensional image, but they may also represent image sequences, short films or a number of different objects according to the angle from which and the light source with which (including moving light sources) etc. they are illuminated. Because of this variety of possible designs, holograms, especially volume holograms, constitute an attractive technical solution for the abovementioned application.

The present invention accordingly further provides for the use of an inventive holographic medium for recording of in-line, off-axis, full-aperture transfer, white light transmission, Denisyuk, off-axis reflection or edge-lit holograms and also of holographic stereograms, in particular for production of optical elements, images or image depictions.

The invention likewise provides holograms comprising the holographic medium of the present invention.

The invention likewise provides a process for producing a hologram wherein pulsed laser radiation is used to expose the medium.

In one embodiment of the process according to the present invention, the pulse duration is ≤200 ns, preferably ≤100 ns, more preferably ≤60 ns. The pulse duration must not be less than 0.5 ns. A pulse duration of 4 ns is particularly preferable.

The present invention further also provides a process for producing a holographic medium by using a photopolymer formulation of the present invention.

The photopolymer formulations can especially be used for production of holographic media in the form of a film. In this case, a ply of a material or material composite transparent to light within the visible spectral range (transmission greater than 85% within the wavelength range from 400 to 780 nm) as carrier substrate is coated on one or both sides, and a cover layer is optionally applied to the photopolymer ply or plies.

Preferred materials or material composites for the carrier substrate are based on polycarbonate (PC), polyethylene terephthalate (PET), polybutylene terephthalate, polyethylene, polypropylene, cellulose acetate, cellulose hydrate, cellulose nitrate, cycloolefin polymers, polystyrene, polyepoxides, polysulphone, cellulose triacetate (CTA), polyamide, polymethylmethacrylate, polyvinyl chloride, polyvinyl butyral or polydicyclopentadiene or mixtures thereof. They are more preferably based on PC, PET and CTA. Material composites may be film laminates or coextrudates. Preferred material composites are duplex and triplex films formed according to one of the schemes A/B, A/B/A or A/B/C. Particular preference is given to PC/PET, PET/PC/PET and PC/TPU (TPU=thermoplastic polyurethane).

The materials or material composites of the carrier substrate may be given an antiadhesive, antistatic, hydrophobized or hydrophilized finish on one or both sides. The modifications mentioned serve the purpose, on the side facing the photopolymer, of making the photopolymer detachable without destruction from the carrier substrate. Modification of the opposite side of the carrier substrate from the photopolymer serves to ensure that the inventive media satisfy specific mechanical demands which exist, for example, in the case of processing in roll laminators, especially in roll-to-roll processes.

The examples which follow serve to elucidate the invention exemplarily without it being restricted thereto.

EXAMPLES

Test Methods:
OH Number:
Reported OH numbers were determined to DIN 53240-2.
NCO Value:
Reported NCO values (isocyanate contents) were determined to DIN EN ISO 11909, Determination of Overhead Temperature:
The overhead temperature was determined in degrees Celsius (° C.) using a 4-20 mA calibrated transmitter and a PT100 thermocouple installed in the boiling equilibrium above a packed column.

Determination of Internal Temperature:
The internal temperature was determined in degrees Celsius (° C.) using a 4-20 mA calibrated transmitter and a PT100 thermocouple installed in the reaction space.

Determination of Diffraction Efficiency in Pulsed Exposure:
To determine the diffraction efficiency in pulsed exposure, the Denisyuk hologram of a mirror was recorded in a sample consisting of a glass plate laminated with a photopolymer film. The substrate of the photopolymer film and the glass substrate faced laser source and the mirror, respectively. The sample was exposed with its planar face perpendicular to the laser beam. The distance between the sample and the mirror was 3 cm.

The laser used was a Brilliant b pulsed laser from Quantel of France. The laser in question was a Q-switched Nd-YAG laser equipped with a module for frequency doubling to 532 nm. The single frequency mode was guaranteed by a seed laser. Coherence length was arithmetically about 1 m. Pulse duration was 4 ns and average power output was 3 watts at a pulse repetition rate of 10 Hz.

The electronically controlled shutter was used to ensure a single pulse exposure. The waveplate made it possible to rotate the polarization plane of the laser light and the subsequent polarizer was used to reflect the S-polarized portion of the laser light in the direction of the sample. The exposed area was adjusted by beam expansion. The waveplate and the beam expander were adjusted such that the sample was given an exposure dose of 100 mJ/cm$^2$/pulse.

To determine the diffraction efficiency, the samples were each exposed with exactly one pulse. After exposure, the sample was bleached on a light table.

Figure 3:
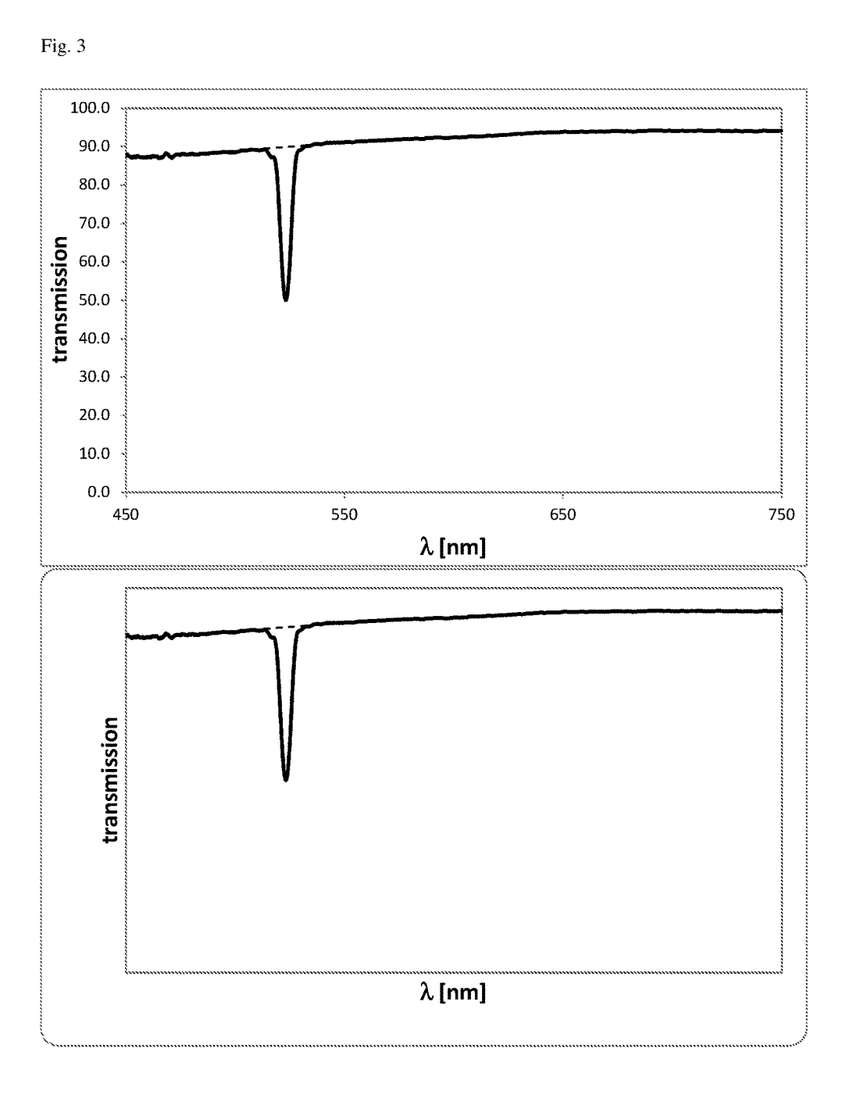

A transmission spectrum was measured through the hologram of the bleached sample. An HR4000 spectrometer from Ocean Optics was used. The sample was placed perpendicularly to the light beam. The transmission spectrum showed a transmission collapse at a wavelength at which the Bragg condition was satisfied. The depth of the transmission collapse to the base line was evaluated as the diffraction efficiency DE of the Denisyuk hologram of the mirror (FIG. 3).

Substances:
The solvents used were obtained commercially.

| | |
|---|---|
| Desmorapid Z | Dibutyltin dilaurate [77-58-7], product from Bayer MaterialScience AG, Leverkusen, Germany. |
| Desmodur ® N 3900 | Product from Bayer MaterialScience AG, Leverkusen, Germany, hexane diisocyanate-based polyisocyanate, proportion of iminooxadiazinedione at least 30%, NCO content: 23.5%. |
| Fomrez UL 28 | Urethanization catalyst, commercial product of Momentive Performance Chemicals, Wilton, CT, USA. |
| Sodium bis(2-ethylhexyl)-sulphosuccinate | [45297-26-5] is available from Aldrich Chemie, Steinheim. |

Compound of the Formula (I)

Example 1

2-Ethylhexyl 4-[4,6-bis(trichloromethyl)-1,3,5-triazin-2-yl]benzoate

Preparation of 2-ethylhexyl 4-cyanobenzoate by the One-Pot Process of the Invention A 25 L jacketed enamelled tank fitted with a glass head, a mechanical stirrer, a distillation head with reflux divider and metering and vacuum units was initially charged under an inert atmosphere with 10.91 kg of 2-ethylhexanol (1.5 eq., [104-76-7] Aldrich Chemie, Steinheim, Germany) at 25° C. and 9.00 kg of methyl 4-cyanobenzoate (1.0 eq., [1129-35-7] ABCR GmbH & CO. KG, Karlsruhe, Germany) were admixed. To this mixture was added 32 g of titanium (IV) 2-ethylhexoxide (0.001 eq., [1070-10-6] ABCR GmbH & CO. KG, Karlsruhe, Germany) and the internal temperature was raised to and maintained at 130° C. for 2 h. During this period, about 1.2 kg of methanol (about ⅔ of the theoretical amount) were distilled. The receiver was emptied and the pressure was reduced to 500 mbar. The internal temperature was raised to and maintained at 135° C. for a further 4 h. At this point in time, no further methanol was collected and, according to analysis by gas chromatography, the reaction mixture no longer contained any methyl 4-cyanobenzoate. The internal temperature was lowered to 100° C., the receiver was emptied and a pressure of 10 mbar was applied. 2-Ethylhexanol was collected at a pressure of 8.8-9.6 mbar and an overhead temperature of 65.5-68.5° C. in an amount of 3.14 kg. After renewed emptying of the receiver, the internal temperature was raised to 185-190° C. and a pressure of 0.25 mbar was applied. 2-Ethylhexyl 4-cyanobenzoate was obtained at an overhead temperature of 150.0-155.0° C. as a colourless oil in an amount of 14.04 kg (96.9% of theory).

GC (column used: 60 m Optima-5 HT MS, temperature programme: $T_{start}$=70° C. for 10 min, then at 3° C./min to 300° C., 300° C. for 5 min) integration in area percent: 0.11% of 2-ethylhexanol, 99.54% of 2-ethylhexyl 4-cyanobenzoate.

$^1$H NMR (400 MHz, CDCl$_3$) δ 8.19-8.08 (m, 2H), 7.79-7.71 (m, 2H), 4.35-4.18 (m, 2H), 1.81-1.65 (hept, J=6.2 Hz, 1H), 1.53-1.23 (m, 8H), 1.01-0.86 (m, 6H).

Preparation of 2-ethylhexyl 4-[4,6-bis(trichloromethyl)-1,3,5-triazin-2-yl]benzoate A 1 L three-necked flask was initially charged with 150.2 g of 2-ethylhexyl 4-cyanobenzoate and 334.4 g of trichloroacetonitrile, and this initial charge was admixed with 15.4 g of aluminium bromide at 0° C. To this mixture was added dried HCl (g) to the point of saturation and then the temperature was raised to 50° C. over 4 h and maintained there for 2 h. Excess HCl (g) was expelled with nitrogen and the reaction mixture was diluted with 100 mL of toluene and kept at −20° C. for 24 h. By-produced tris(trichloromethyl)-1,3,5-triazine separates out quantitatively at this temperature and the supernatant solution was decanted. The solvent was removed under reduced pressure to leave 256 g of a slightly pale yellow oil.

$^1$H NMR (400 MHz, CDCl$_3$) δ 8.81-8.71 (m, 2H), 8.28-8.20 (m, 2H), 4.36-4.25 (m, 2H), 1.81-1.70 (dt, J=12.2, 6.1 Hz, 1H), 1.53-1.39 (m, 11H), 1.39-1.27 (m, 4H), 1.05-0.95 (t, J=7.5 Hz, 3H), 0.95-0.87 (m, 3H).

$^{13}$C NMR (101 MHz, CDCl$_3$) δ 175.42, 174.09, 165.72, 137.00, 135.85, 130.15, 129.97, 94.74, 67.98, 38.93, 30.61, 28.99, 26.90, 24.03, 22.96, 14.03, 11.11.

Preparation of Further Components for the Photopolymer Formulation:

Preparation of Polyol 1:

A 1 l flask was initially charged with 0.18 g of tin octoate, 374.8 g of ε-caprolactone and 374.8 g of a difunctional polytetrahydrofuran polyether polyol (equivalent weight 500 g/mol OH), which were heated to 120° C. and kept at this temperature until the solids content (proportion of nonvolatile constituents) was 99.5% by weight or higher. Subsequently, the mixture was cooled and the product was obtained as a waxy solid.

Preparation of Urethane Acrylate 1 (Writing Monomer): Phosphorothioyltris(oxybenzene-4,1-diylcarbamoyloxyethane-2,1-diyl) Trisacrylate A 500 mL round-bottom flask was initially charged with 0.1 g of 2,6-di-tert-butyl-4-methylphenol, 0.05 g of dibutyltin dilaurate (Desmorapid® Z, Bayer MaterialScience AG, Leverkusen, Germany) and 213.07 g of a 27% solution of tris(p-isocyanatophenyl) thiophosphate in ethyl acetate (Desmodur® RFE, product from Bayer MaterialScience AG, Leverkusen, Germany), which were heated to 60° C. Subsequently, 42.37 g of 2-hydroxyethyl acrylate were added dropwise and the mixture was still kept at 60° C. until the isocyanate content had fallen below 0.1%. This was followed by cooling and complete removal of the ethyl acetate under reduced pressure. The product was obtained as a semicrystalline solid.

Preparation of Urethane Acrylate 2 (Writing Monomer): 2-({[3-(Methylsulphanyl)phenyl]-carbamoyl}oxy)ethyl prop-2-enoate

A 100 mL round-bottom flask was initially charged with 0.02 g of 2,6-di-tert-butyl-4-methylphenol, 0.01 g of Desmorapid® Z, 117 g of 3-(methylthio)phenyl isocyanate [28479-1-8], and the mixture was heated to 60° C. Subsequently, 8.2 g of 2-hydroxyethyl acrylate were added dropwise and the mixture was still kept at 60° C. until the isocyanate content had fallen below 0.1%. This was followed by cooling. The product was obtained as a colourless liquid.

Preparation of Additive 1 bis(2,2,3,3,4,4,5,5,6,6,7,7-dodecafluoroheptyl)(2,2,4-trimethylhexane-1,6-diyl) Biscarbamate

A 50 mL round-bottom flask was initially charged with 0.02 g of Desmorapid® Z and 3.6 g of 2,4,4-trimethylhexane 1,6-diisocyanate (TMDI), and the mixture was heated to 60° C. Subsequently, 11.9 g of 2,2,3,3,4,4,5,5,6,6,7,7-dodecafluoroheptan-1-ol were added dropwise and the mixture was still kept at 60° C. until the isocyanate content had fallen below 0.1%. This was followed by cooling. The product was obtained as a colourless oil.

Preparation of Dye 1:

In a procedure similar to Example 6 of DE 1 073 662, 6.98 g of the cyanomethylene base of the formula and 6.16 g of the aldehyde of the formula in 30 mL of anhydrous toluene were gradually admixed with 3.57 g of thionyl chloride under agitation. This was followed by stirring at 100° C. for 1 h and cooling. 50 mL of toluene were added and the dye was filtered off with suction. The dye was stirred up three times with 30 mL of toluene each time and again filtered off with suction each time. After drying at 50° C. under reduced pressure, the red dye was substantially dissolved in 100 mL of water. A solution of 12.38 g of sodium bis(2-ethylhexyl)sulphosuccinate in 100 mL of butyl acetate was added. The two-phase mixture was stirred for 1 h and then transferred into a separating funnel. The aqueous phase was dropped and the organic phase was washed four times with 40 mL of water. After removal of the last wash liquor, the organic phase was diluted with 250 mL of butyl acetate and distilled water-free in a rotary evaporator under reduced pressure. About 200 mL of butyl acetate were also distilled off in the process, to finally leave 150.1 g of a red solution of the dye of the formula in butyl acetate, said solution being storage stable.

A sample was taken and the remaining solvent was stripped off under reduced pressure. After drying at 50° C. under reduced pressure, the dye was obtained as a red resinous substance. $\lambda_{max}$ (in $CH_3CN$)=498 nm and 523 nm, $\varepsilon$=89580 (at 498 nm) and 99423 L $mol^{-1}$ $cm^{-1}$ (at 523 nm) L $mol^{-1}$ $cm^{-1}$. These spectroscopic data showed the concentration of the above solution to be 10.0%.

Production of Media to Determine the Holographic Properties

Production of Holographic Media on a Foil-coating Range

A continuous process will now be described for producing holographic media in the form of films from inventive and non-inventive photopolymer formulations.

Figure 1:
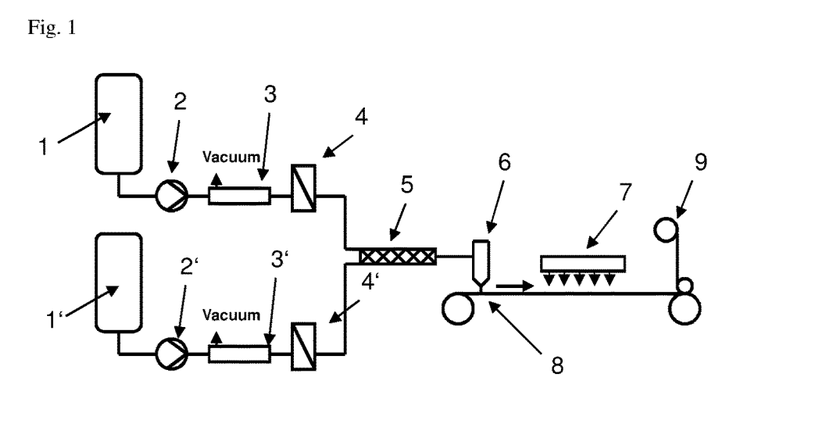

The production process was carried out using the foil-coating range depicted in FIG. 1, wherein the individual component parts are assigned the following reference symbols. FIG. 1 shows the schematic set-up of the coating range used. In said figure, the individual component parts have the following reference signs:

1, 1' stock reservoir vessel
2, 2' metering device
3, 3' vacuum degassing device
4, 4' filter
5 static mixer
6 coating device
7 circulating air dryer
8 carrier substrate
9 covering layer Example Medium 1

To prepare the photopolymer formulation, 39.42 g of polyol 1 were incrementally admixed with a mixture of 15.00 g of urethane acrylate 1 and 15.00 g of urethane acrylate 2, 11.25 g of additive 1, 0.075 g of Example 1, 0.75 g of CGI 909, 0.68 g of BYK® 310 surfactant, 0.038 g of Fomrez UL-28 and 23.65 g of ethyl acetate and homogenized. The mixture was subsequently admixed with 1.50 g of a 10% solution of dye 1 in ethyl acetate in the dark and homogenized so that a clear solution was obtained. If necessary, the formulation was briefly heated at 60° C. to speed up the dissolving of the materials used. This mixture was imported into one of the two stock reservoir vessels 1 of the coating range. Into the second stock reservoir vessel 1' was filled the polyisocyanate component (Desmodur® N 3900, commercial product of Bayer MaterialScience AG, Leverkusen, Germany, polyisocyanate based on hexane diisocyanate, at least 30% proportion of iminooxadiazinedione, NCO content: 23.5%). The two components were then each fed through the metering devices 2 in a ratio of 942.2 (component mixture) to 57.8 (isocyanate) to the vacuum degassing device 3 and degassed. From there they were then each passed through the filters 4 into the static mixer 5, where the components were mixed to form the photopolymer formulation. The liquid material obtained was then sent to the coating device 6.

The coating device 6 in the present case was a doctor blade system known to a person skilled in the art. Alternatively, however, it is also possible to use a slot die. Said coating device 6 was used to apply the photopolymer formulation at a processing temperature of 20° C. to a carrier substrate 8 in the form of a 36 μm thick polyethylene terephthalate foil and dried in a circulating air dryer 7 at a crosslinking temperature of 80° C. for 5.8 minutes to obtain a medium in the form of a film which was then provided a 40 μm thick polyethylene foil as covering layer 9 and wound up.

The desired target layer thickness of the film was preferably between 1 and 60 μm, preferably from 5 to 25 μm, more preferably from 10 to 15 μm.

The production speed was preferably in the range from 0.2 m/min to 300 m/min and more preferably in the range from 1.0 m/min to 50 m/min.

The layer thickness obtained for the film was 12 μm±1 μm.

Comparative Medium I

Comparative medium I was without Example 1 as described above.

Figure 2:
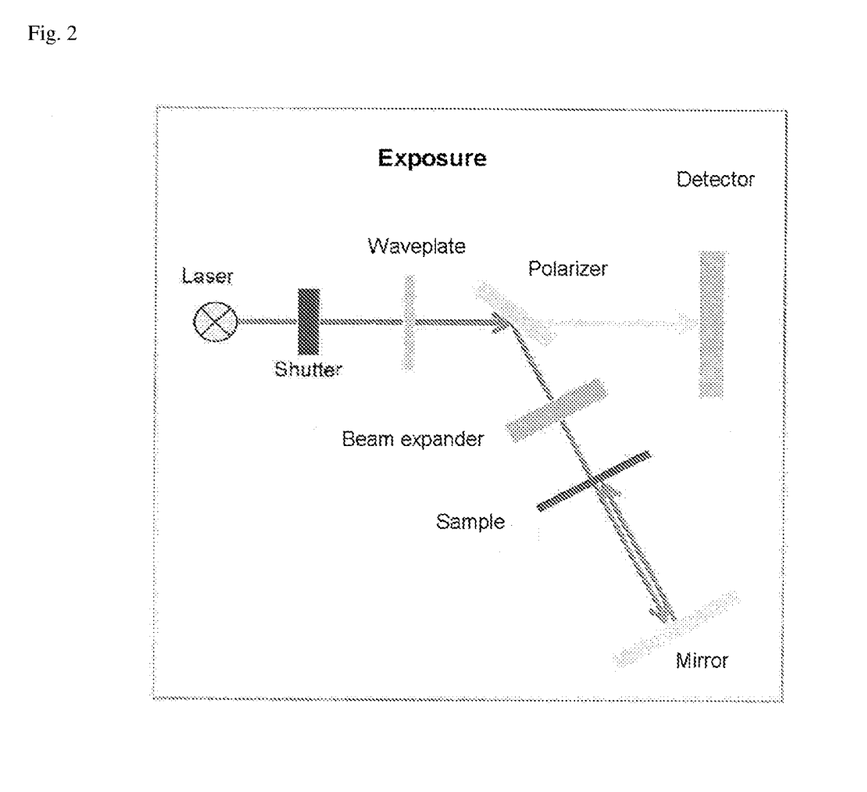

Holographic Testing:

The media obtained as described were tested for their holographic properties by using a measuring arrangement as per FIG. 2 in the manner described above (Determination of diffraction efficiency in pulsed exposure). The following measurements were obtained for DE at a fixed dose of 100 mJ/cm$^2$:

TABLE 1

Holographic assessment of selected examples

| Example medium | Single pulse DE [%] |
|---|---|
| 1 | 49 |

TABLE 2

Holographic assessment of selected comparative media

| Comparative medium | Single pulse DE [%] |
|---|---|
| I | 2% |

The value found for Example medium 1 shows that the inventive formula (I) compounds used in the photopolymer formulations are very useful in holographic media to be exposed with pulsed laser. Comparative medium I is free from any formula (I) compound according to the invention and is unsuitable for use in holographic media to be exposed with pulsed laser.

The invention claimed is:

1. A process for producing para-disubstituted benzonitriles of formula (IV)

wherein $R^1$, $R^2$, $R^3$ and $R^4$ are each independently hydrogen, halogen, alkyl, alkoxy, alkenyl, alkynyl, alkylthio, alkylseleno, wherein $R^1$ and $R^2$ and/or $R^3$ and $R^4$ may combine to form a 3 to 5-membered saturated or unsaturated bridge optionally substituted with up to 2 heteroatoms and $R^5$ is linear $C_5$ to $C_{20}$ alkyl which is optionally substituted in any manner by halogen and/or $C_1$ to $C_{10}$ alkyl and/or $C_1$ to $C_{10}$ alkoxy and in which up to six carbon atoms may be replaced by oxygen, in which case at least two carbon atoms shall be present between two oxygen atoms and the $R^5$ moiety starts with at least two carbon atoms, wherein the terminal methyl group of the linear $C_5$ to $C_{20}$ alkyl moiety shall be unsubstituted and $R^6$ is methyl, ethyl or isomeric propyl, and A is a catalyst A, in a one-pot process wherein component (III) is used in excess, components (V), (III) and (IV) are distillatively removed in the stated order in three steps by adjusting the pressure and the temperature, and the difference in the boiling points of compounds (V) and (III) and in the boiling points of compounds (III) and (IV) is not less than 50° C. in either case;

wherein said catalyst A is a titanium(IV) or zirconium(IV) alkanoate wherein the alkanoate corresponds to that of compound (III).

* * * * *